United States Patent
Robins et al.

(10) Patent No.: US 7,105,322 B2
(45) Date of Patent: Sep. 12, 2006

(54) PROCESS FOR THE PREPARATION OF AMIDES

(75) Inventors: Karen Tracey Robins, South Guangzhou (CN); Toru Nagasawa, Kurono (JP)

(73) Assignee: Lonza AG, Basel (CH)

( * ) Notice: Subject to any disclaimer, the term of this patent is extended or adjusted under 35 U.S.C. 154(b) by 209 days.

(21) Appl. No.: 10/234,088

(22) Filed: Sep. 3, 2002

(65) Prior Publication Data

US 2003/0148478 A1 Aug. 7, 2003

Related U.S. Application Data

(62) Division of application No. 09/463,203, filed on Mar. 27, 2000, now Pat. No. 6,444,451.

(30) Foreign Application Priority Data

Jul. 22, 1997 (CH) ................................. 1776/97
Nov. 17, 1997 (CH) ................................. 2629/97
Apr. 6, 1998 (CH) ................................. 0815/98

(51) Int. Cl.
*C12P 13/02* (2006.01)
*C12N 1/20* (2006.01)

(52) U.S. Cl. .................. 435/129; 435/170; 435/252.1; 435/822

(58) Field of Classification Search ................ 435/129, 435/170, 252.1, 822
See application file for complete search history.

(56) References Cited

U.S. PATENT DOCUMENTS 5,200,331 A 4/1993 Kawakami et al.
6,444,451 B1 * 9/2002 Robins et al. .............. 435/129

FOREIGN PATENT DOCUMENTS

| | | |
|---|---|---|
| EP | 0188316 | 7/1986 |
| EP | 0307926 | 3/1989 |
| EP | 0362829 | 11/1990 |
| GB | 2290295 | 12/1995 |
| WO | WO 9517505 | 6/1995 |

OTHER PUBLICATIONS

Wakamoto et al., Mar. 24, 1994, *Chemical Abstracts* 120(13):161780.

* cited by examiner

*Primary Examiner*—Herbert J. Lilling
(74) *Attorney, Agent, or Firm*—Baker Botts LLP

(57) ABSTRACT

A novel biotechnological process for the preparation of nitriles, starting from amides, is described. Micro-organisms of the genus *Amycolatopsis*, *Actinomadura* or *Rhodococcus* are employed for this process.

10 Claims, 9 Drawing Sheets

PROCESS FOR THE PREPARATION OF AMIDES

This application is a divisional of 09/463,203, filed Mar. 27, 2000, now U.S. Pat. No. 6,444,451, which is a national phase application under 35 U.S.C. §371 of International Application No. PCT/EP98/04587, incorporated by reference herein, which was filed on Jul. 22, 1998 and published in German on Feb. 4, 1999.

The invention relates to novel microorganisms of the genus *Actinomadura, Amycolatopsis* or *Rhodococcus*, and to a novel process for the preparation of amides using these microorganisms or using enzyme extracts of these microorganisms.

For amides such as, for example, nicotinamide, a vitamin of the vitamin B complex which is essential to animals and man, a number of biotechnological processes are already known. Generally, it is known that microorganisms containing nitrile hydratase convert nitriles to the corresponding amides. Thus EP-A-0 188 316 describes a process for the preparation of nicotinamide starting from 3-cyanopyridine using microorganisms of the genus *Rhodococcus, Arthrobacter* or *Microbacterium*.

A disadvantage of this process is that these micro-organisms have only a low activity for the conversion of 3-cyanopyridine to nicotinamide.

EP-A-0 307 926 describes the conversion of 3-cyanopyridine to nicotinamide by means of microorganisms of the species *Rhodococcus rhodochrous* J1. In order that these microorganisms catalyse the desired conversion, they must be induced.

A further disadvantage of this process is that *Rhodococcus rhodochrous* J1 is red-coloured and accordingly a discoloration of the product takes place. In addition, this microorganism has a low heat stability and is inhibited, for example, by the substrate 3-cyano-pyridine.

A further process for the preparation of nicotinamide starting from 3-cyanopyridine by means of microorganisms of the species *Rhodococcus rhodochrous* J1 is described in EP-A-0 362 829. In order to increase the specific activity of the microorganisms containing nitrile hydratase, urea or a urea derivative was added to the culturing medium as an inducer. As in the process described beforehand, a discoloration of the product also takes place in this process.

In addition, WO 95/17 505 describes a process for the preparation of aromatic amides starting from the corresponding nitriles by means of microorganisms of the species *Rhodococcus rhodochrous* M33. A disadvantage of this process is the red colouration of *Rhodococcus rhodochrous* M33 and also the high $K_M$ value for the substrate 3-cyanopyridine.

The object of the present invention was to eliminate these disadvantages and to make available a process for the preparation of amides in which the corresponding amides can be isolated in good yield and purity.

This object is achieved by the novel microorganisms according to claims 1 and 3, and by the process according to claim 6.

According to the invention, the process is carried out by converting a nitrile, as substrate, to the corresponding amide by means of microorganisms of the genus *Actinomadura, Amycolatopsis* or *Rhodococcus*, using an enzyme extract of these microorganisms or by means of purified nitrile hydratase of microorganisms of the genus *Amycolatopsis* or *Actinomadura*.

The nitriles employed for the biotransformation such as, for example, 3-cyanopyridine are commercially available compounds.

The microorganisms according to the invention are able to convert nitriles as substrates into the corresponding amides. Preferably, these microorganisms have the ability to grow on nitriles or amides as the sole C and/or N source.

The microorganisms according to the invention are obtainable by means of suitable selection, for example, from soil samples, sludge or waste water with the aid of customary microbiological techniques. Expediently, the microorganisms are selected by growth with nitriles or amides as the preferably sole C and N source in the presence of cobalt ions. Nitriles and amides suitable for selection are, in particular, the nitriles also employed as substrates in the later biotransformation and the corresponding amides obtainable therefrom. Suitable growth media are likewise known to the person skilled in the art, for example the medium described in Table 1 can be used.

Customarily, the microorganisms are cultured (grown) in the same manner even before the actual biotransformation, the abovementioned media being used.

As known professionally, a nitrile hydratase is only formed when the growth medium contains cobalt ions as a cofactor. Suitable "cobalt compounds generating cobalt ions" are $Co^{2+}$ or $Co^{3+}$ salts. Examples of $Co^{2+}$ and $Co^{3+}$ salts are cobalt chlorides, cobalt sulphates and cobalt acetates.

Expediently, the cobalt compound employed is a $Co^{2+}$ salt such as, for example, $CoCl_2$. Growth, however, can also be carried out in the presence of vitamin B12 together with metallic cobalt or other cobalt compounds which generate a cobalt ion in situ. Expediently, the cobalt compound is employed in an amount from 1 to 10 mg/l, preferably from 1 to 3 mg/l.

Customarily, growth is carried out at a temperature from 20 to 50° C. and at a pH between pH 5 and pH 8, preferably from 30 to 45° C. and between pH 5.5 and pH 7.5.

The actual biotransformation can be carried out using microorganisms of the genus *Actinomadura, Amycolatopsis*, using an enzyme extract of these microorganisms or by means of purified nitrile hydratase from these microorganisms. Expediently, the biotransformation is carried out using microorganisms of the species *Actinomadura* spadix, for example the isolates *Actinomadura* spadix E3733, *Actinomadura* spadix E3736, *Actinomadura* spadix 45A32, *Actinomadura* spadix 4501 or *Actinomadura* spadix C15. The biotransformation is preferably carried out using microorganisms corresponding to the species Amycolatopsis NE 31 and Amycolatopsis NA40 or their functionally equivalent variants and mutants. Micro-organisms corresponding to the species Amycolatopsis NA40 are particularly preferably employed. Microorganisms of the species mentioned were deposited on 03.06.1997 in the Deutschen Sammlung von Mikroorganismen und Zellkulturen GmbH [German Collection of Microorganisms and Cell Cultures GmbH], Mascheroderweg 1b, D-38124 Brunswick under the designations Amycolatopsis NE 31 and Amycolatopsis NA40 according to the Budapest Convention and have the deposit numbers DSMZ 11616 and DSMZ 11617 respectively. These two microorganisms have been more accurately identified and are to be assigned to species of the genus *Amycolatopsis* which have not yet been described in the literature.

Accordingly, the invention also relates to microorganisms of the genus Amycolatopsis or *Actinomadura* which are capable of converting an amide into a nitrile, in particular microorganisms with the designation Amycolatopsis NA40 (DSMZ 11617) and Amycolatopsis NE31 (DSMZ 11616).

In addition, it has been found that specific microorganisms of the genus *Rhodoccus* have better properties for the conversion of nitriles to amides than the *Rhodococcus rhodochrous* J1 described in EP-A-0 362 829. These microorganisms are *Rhodoccus* GF674, *Rhodoccus* GF578, *Rhodoccus* GF473, *Rhodoccus* GF270 (DSMZ 12211) and *Rhodoccus* GF376 (DSMZ 12175) or their functionally equivalent variants and mutants. The microorganism DSMZ 12175 was deposited on 15.5.1998 and the microorganism DSMZ 12211 on 8.6.1998 in the Deutschen Sannlung von Mikroorganismen und Zellkulturen GmbH [German Collection of Microorganisms and Cell Cultures GmbH] according to the Budapest Convention.

The *Rhodoccus* strains GF270, GF376, GF473, GF578 and GF674 have been assigned according to identification to species of the genus *Rhodoccus* which are not yet described in the literature. Accordingly, the invention also relates to the microorganisms *Rhodoccus* GF270, *Rhodoccus* GF376, *Rhodoccus* GF473, *Rhodoccus* GF578 and *Rhodoccus* GF674.

Unlike the microorganisms of the genus *Actinomadura* or Amycolatopsis, the microorganisms of the genus *Rhodoccus* are expediently induced before the actual conversion. Suitable inducers are those described in EP-A-0 307 926, such as, for example, acetamide, butyramide, methacrylamide, propionamide, crotonamide and valeramide.

"Functionally equivalent variants and mutants" is understood as meaning microorganisms which are derived from the abovementioned source organisms and essentially have the same characteristics and functions as these. Variants and mutants of this type can be formed by chance, e.g. by UV irradiation or by mutagenic chemicals.

| Identification of Amycolatopsis NA40 | |
| --- | --- |
| Colour of aerial mycelium | white |
| Colour of substrate mycelium | orange |
| Colour of diffused pigment | – |
| Sugar spectrum | |
| ARA | + |
| GAL | + |
| MAD | – |
| XYL | – |
| GLU | tr |
| RIB | + |
| Type | A |
| DAP | DL |
| Menaquinones (in %) | |
| 8/4 | – |
| 9/0 | (+) |
| 9/2 | + |
| 9/4 | +++ |
| 9/6 | – |
| 9/8 | – |
| 16S rDNA homology | 96.9% |
| Phospholipids such as PE, OH-PE, lyso PE, met PE, PC, NPG, PI, PIM, PG, DPG, GL | not investigated |
| Fatty acids | |
| iso 16 | +++ |
| iso 15 | + |
| iso 17 | (+) |
| anteiso 15 | (+) |
| anteiso 17 | (+) |
| 10-Me 16 | – |
| 10-Me 17 | + |
| 2-OH 15 | + |
| 2-OH 16 | + |
| Type | 3f |
| MS | – |
| Identification of Amycolatopsis NE31 | |
| Colour of aerial mycelium | white |
| Colour of substrate mycelium | orange |
| Colour of diffused pigment | – |
| Sugar spectrum | |
| ARA | + |
| GAL | + |
| MAD | – |
| XYL | – |
| GLU | tr |
| RIB | + |
| Type | A |
| DAP | DL |
| Menaquinones (in %) | |
| 8/4 | – |
| 9/0 | (+) |
| 9/2 | + |
| 9/4 | +++ |
| 9/6 | – |
| 9/8 | – |
| 16S rDNA homology | 96.1% |
| Phospholipids such as PE, OH-PE, lyso PE, met PE, PC, NPG, PI, PIM, PG DPG, GL | not investigated |
| Fatty acids | |
| iso 16 | +++ |
| iso 15 | + |
| iso 17 | (+) |
| anteiso 15 | (+) |
| anteiso 17 | (+) |
| 10-Me 16 | – |
| 10-Me 17 | + |
| 2-OH 15 | + |
| 2-OH 16 | + |
| Type | 3f |
| MS | – |
| Abbreviations and explanations for the identification | |
| (+) | 1–5% |
| + | 5–15% |
| ++ | 15–30% |
| +++ | >30% |
| DAP | diaminopimelic acid |
| ARA | arabinose |
| GAL | galactose |
| MAD | madurose |
| XYL | xylose |
| GLU | glucose |
| RIB | ribose |
| Sugar types according to Lechevalier et al. 1971 | |
| Fatty acid types according to Kroppenstedt 1985 and 1992. | |
| 9/4 | MK-9 ($H_4$) |
| 9/6 | MK-9 ($H_6$) |
| 9/8 | MK-9 ($H_8$) |
| MS | mycolic acids |
| PE | phosphatidylethanolamine |
| OH-PE | hydroxy-PE |
| met PE | phosphatidimethylethanolamine |
| PC | phosphatidylcholine |
| NPG | phosphatidylglucosamine |
| PI | phosphatidylinositol |
| PIM | phosphatidylinositol mannoside |
| PG | phosphatidylglycerol |
| DPG | diphosphatidylglycerol |
| GL | glycolipids |

-continued

| Fatty acids | |
|---|---|
| iso-16 | isohexadecanoic acids or 14-methylpentadecanoic acids |
| 10-Me-18 | tuberculostearic acid |
| 2-OH-16 | 2-hydroxypalmitic acid |

Identification of GF270, GF376, GF473, GF578 and GF674 The identification of these strains is based on 5 characteristics which are independent of one another.
1. Morphology and colour of the colonies: short-branched hyphae, which disintegrate into rod- and spore-like elements. The colonies of GF270 and GF376 are salmon-pink (RAL 3022) and those of GF578 and GF674 are light red (RAL 3012).
2. Diamino acids of the peptidoglycan: meso-diaminopimelic acid
3. Mycolic acids: *Rhodoccus* mycolic acids: The determination of the long-chain mycolic acid was carried out by means of high-temperature gas chromatography. The elution profiles of the mycolic acids of GF270 and GF376 and those of GF473, GF578 and GF674 were identical. The mycolic acid length for GF270 and GF376 was $C_{38}$–$C_{46}$ and that for GF473, GF578 and GF674 was $C_{40}$–$C_{48}$. The mycolic acid patterns were compared with mycolic acid patterns of *Rhodoccus* strains. GF270 was identified with a very low correlation factor (0.086) as belonging to *Rhodococcus rhodochrous*; it was not possible to identify GF376 by this method. The other three isolates GF473, GF578 and GF674 were identified with a very low correlation factor as belonging to *Rhodoccus ruber*.
4. Fatty acid pattern: unbranched, saturated and unsaturated fatty acids including tuberculostearic acid. The fatty acid pattern is diagnostic of all *Rhodococcus* genera and closely related *Mycobacterium*, Nocardia, Dietzia, Tsukamurella and some Corynebacteria species. The identification at the species level was obtained by qualitative and quantitative differences in the fatty acid pattern of GF270, GF376, GF473, GF578 and GF674 with the fatty acid patterns of *Rhodoccus* species.
5. The 16S rDNA subsequences of GF270 and GF376 were identical (100%), although the comparison of them with the *Rhodoccus* strains only showed 99.1% similarity to the closest related *Rhodococcus rhodochrous*. GF473 and GF578 were identical in their 16S rDNA sequence (100%). GF674 differs from GF578 in only one base pair of 500 (99.8%). All three isolates show only a distant relationship with *Rhodoccus coprophilus* (98.4%). Based on the chemotaxic and molecular biology results, it can be concluded that GF270 and GF376 on the one hand and GF473, GF578 and GF674 on the other hand are strains of 2 new *Rhodoccus* species. GF270 and GF376 are closely related to *Rhodococcus rhodochrous* in their 16S rDNA (99.1%), however GF473, GF578 and GF674 are only distantly related to *Rhodoccus coprophilus* (98.4%).

The enzyme extract can be obtained by professionally customary disruption of the microorganisms, such as, for example, by disruption by means of ultrasound, by means of the French press method or the lysozyme method. This enzyme extract and, of course, also the complete microorganism cells can be immobilized on a suitable support material, customarily embedded in a polymer, for carrying out the process, or absorbed on a suitable support material.

The enzymes according to the invention having nitrile hydratase activity are obtainable from the microorganisms of the genus Amycolatopsis and are able to convert a nitrile into an amide, in particular they are obtainable from Amycolatopsis NA40 (DSMZ 11617).

These enzymes in particular have the following properties:
a) a pH optimum of pH 6.5±1.0
b) a temperature optimum between 35 and 40° C. at a pH of 7.0
c) a $K_M$ value for the substrate 3-cyanopyridine of 41.7 mM±7.7 mM (20° C., 45 mM phosphate buffer, pH 7.0)

in particular the enzymes have a
d) molecular weight of 106 kDa, such as, for example, determined by SDS-PAGE.

Nitriles can generally be employed as substrates for the biotransformation. Expediently, either aliphatic nitriles having 1 to 10 carbon atoms, optionally substituted by, for example, hydroxyl, amino, halogen or carboxyl, or substituted or unsubstituted aromatic nitriles having 4 to 10 carbon atoms in the aromatic ring system are employed. Aliphatic nitriles having 1 to 10 carbon atoms which can be used are dinitriles, hydroxynitriles, aminonitriles such as, for example, n-octanenitrile, cyanoacetic acid, isocapronitrile, n-valeronitrile, adiponitrile, glutaronitrile, succinonitrile, sebaconitrile, propionitrile, crotononitrile, acrylonitrile, methacrylonitrile, n-butyronitrile or azelanitrile. Aromatic nitriles having 4 to 10 carbon atoms which can be used are nitriles of the general formula

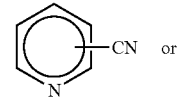

I

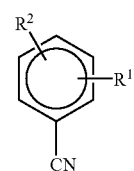

II in which $R^1$ and $R^2$ are a hydrogen atom, a halogen atom or $C_{1-4}$-alkyl. F, Cl, Br or I can be used as halogen atom. Methyl, ethyl, propyl, isopropyl, tert-propyl, butyl, isobutyl or tert-butyl can be used as $C_{1-4}$-alkyl. Expedient representatives of the aromatic nitriles of the general formula I or II are 2-, 3- or 4-cyanopyridine, benzonitrile, fluoro-, chloro- or bromobenzonitrile, such as, for example, o-, m- or p-chlorobenzonitrile or 2-chloro-3-cyanopyridine. 3-Cyanopyridine is preferably used as aromatic nitrile having 4 to 10 carbon atoms.

The biotransformation is expediently carried out with addition of substrate in one portion or continuously such that the substrate concentration does not exceed 40% by weight, preferably 30% by weight.

The process is expediently carried out with resting (non—growing) cells.

Suitable media for the biotransformation are those customary in the specialist field, such as, for example, low molecular weight phosphate buffers, HEPES buffers, citrate buffers, borate buffers, the media according to Tables 1 to 3 or modified forms thereof such as, for example, those described in Example 8 (1) or TRIS/HCl buffers.

The biotransformation is expediently carried out at a temperature from 0 to 50° C. and at a pH between pH 4.5 and pH 10, preferably at a temperature from 20 to 40° C. and at a pH between pH 4.5 and pH 10.0.

In a particularly preferred embodiment, the biotransformation can be carried out in the presence of $C_{1-4}$-alcohols.

$C_{1-4}$-alcohols employed can be methanol, ethanol, propanol or butanol. Methanol is preferably used.

After the reaction, the corresponding amides can then be isolated by customary working-up methods such as, for example, by crystallization.

EXAMPLES

Example 1

Growth of Microorganisms of the Genus *Actinomadura* or Amycolatopsis a) Various soil samples were inoculated with various nitriles or amides as a C and N source in the enrichment medium according to Table 1 and incubated at 37° C. or 45° C. for 7–10 days. The cultures were then transferred to the same medium and again cultured at 37° C. for 7–10 days. The whole process was repeated 3 times. The cultures were then diluted and plated out in order to obtain individual colonies. The plates were incubated at 37° C. for 5 days. The different colonies were then tested for the desired activity.

Amycolatopsis NA40 (DSMZ 11617) and Amycolatopsis NE31 (DSMZ 11616) were isolated in this way and then grown in the optimized medium (Table 3) for 90–100 h with shaking at 37° C.

Adiponitrile served as a C and N source for Amycolatopsis NE31 (DSMZ 11616), *Actinomadura* spadix E3733 and *Actinomadura* spadix E3736, azelanitrile served as a C and N source for Amycolatopsis NA40 (DSMZ 11617) and *Actinomadura* spadix 45A32, n-octanenitrile served as a C and N source for *Actinomadura* spadix 4501 and cyanoacetic acid served as a C and N source for *Actinomadura* spadix C15.

b) Amycolatopsis NA40 was cultured in the medium according to Table 3. The culturing was carried out for 2 or 3 to 4 days at a temperature of 37° C. under measured turbidimetrically at 610 nm and the dry weight of the cells was calculated in the following way: weight of the dry cells in mg/ml=$OD_{610\ nm}$ ×0.277.

TABLE 1

| Enrichment medium | |
|---|---|
| Nitrile | 2.0 g |
| $KH_2PO_4$ | 7.0 g |
| $MgSO_4.7H_2O$ | 0.1 g |
| Vitamin mixture | 1.0 ml |
| $CoCl_2.6H_2O$ | 2.0 mg |
| $FeSO_4.7H_2O$ | 2.0 mg |

Make up to 1 l with water (pH 6.7–7.3)

TABLE 2

| Basal medium | |
|---|---|
| Maltose | 2.0 g |
| $NaNO_3$ | 1.0 g |
| $K_2HPO_4$ | 0.1 g |
| $MgSO_4.7H_2O$ | 0.05 g |

Make up to 100 ml with water (pH 7.0)

TABLE 3

| Optimized medium | |
|---|---|
| D-glucose | 4.5 g |
| Meat extract | 0.5 g |
| $K_2HPO_4$ | 0.1 g |
| $MgSO_4.7H_2O$ | 0.05 g |
| $CoCl_2.6H_2O$ | 1.0 mg |

Make up to 100 ml with water (pH 7.0)

Example 2

Biotransformations with Microorganisms of the Genus *Actinomadura* or Amycolatopsis (1) For determination of the nitrile hydratase activity, a reaction mixture (2 ml) containing 3-cyanopyridine (1.0 M, 1.0 ml), potassium phosphate buffer (pH 7.0, 0.1 M, 0.5 ml) and 0.5 ml of cell suspension were incubated at 20° C. for 30 min with stirring. The reaction was stopped by addition of 0.2 ml of 3 N HCl. After centrifuging briefly, the nicotinamide formed was determined by means of HPLC (Shimadzu SPD 6A system using a C18 column (Develosil ODS-HG-5, 4.6×250 cm); eluent: 10 mM $KH_2PO_4/H_3PO_4$ (pH 2.8)/acetonitrile 9:1 (v/v); flow rate: 1 ml/min; the absorption was measured at 230 nm). The specific activity was expressed as μmol of nicotinamide formed/ml/min/$OD_{610\ nm}$.

The reaction rates of aliphatic nitriles in the enrichment medium (Table 1) with isolated bacteria is summarized in Table 5, the effects of inducers and cofactors in the basal medium (Table 2) is summarized in Table 4 and the activity comparison of Amycolatopsis to *Rhodoccus* in the basal medium (Table 2) is summarized in Table 6. The results from Table 4 show that the nitrile hydratase from Amycolatopsis NA40 is constitutively expressed but the cofactor cobalt is necessary for the activity.

(2) Effect of the Temperature on the Growth of NA40

Subcultures (2 ml) were incubated at 37° C. for 2 days in the medium according to Table 3, and then transferred to shaker flasks containing 20 ml of medium according to Table 3. Culturing was carried out at 37, 40, 45, 50 and 55° C. for 3 to 4 days with shaking. The cell growth was measured and the nitrile hydratase activity was determined at 20° C. Table 7 shows the effect of the temperature on the nitrile hydratase activity and on the cell growth.

TABLE 4

Effects of Inducers and cofactors on the specific activity in the basal medium

| | Growth ($OD_{610\ nm}$) | Total activity (μmol/ml/min) | Specific activity (μmol/ml/min/OD) |
|---|---|---|---|
| Inducer | | | |
| — | 1.26 | 20.9 | 16.6 |
| ε-Caprolactam | 0.66 | 9.52 | 14.5 |
| Crotonamide | 3.41 | 22.9 | 6.72 |
| Methacrylamide | 3.33 | 2.46 | 0.74 |
| Butyramide | 2.19 | 0.19 | 0.88 |
| Propionamide | 1.91 | 0.92 | 0.48 |
| Urea | 1.72 | 2.97 | 1.73 |
| Cofactor | | | |
| — | 7.97 | 0.10 | 0.01 |
| $FeSO_4.7H_2O$ | 8.32 | 3.36 | 0.40 |
| $CoCl_2.6H_2O$ | 8.41 | 47.8 | 5.68 |

TABLE 5

Conversion rates of aliphatic nitriles using the isolated bacteria

| | Strains | Substrates | Growth (OD$_{610\,mm}$) | Total activity (μmol/ml/min) | Specific activity (μmol/ml/min/OD) |
|---|---|---|---|---|---|
| Amycolatopsis | NE31 (DSMZ 11616) | Adiponitrile | 2.68 | 0.377 | 0.141 |
| Actinomadura spadix | E3733 | Adiponitrile | 1.62 | 0.347 | 0.214 |
| Actinomadura spadix | E3736 | Adiponitrile | 1.36 | 3.00 | 2.21 |
| Actinomadura spadix | 45A32 | Azelanitrile | 5.81 | 18.8 | 3.23 |
| Actinomadura spadix | 45O1 | n-octane-nitrile | 7.24 | 32.2 | 4.45 |
| Actinomadura spadix | C15 | Cyanoacetic acid | 2.04 | 7.01 | 3.43 |
| Amycolatopsis | NA40 (DSMZ 11617) | Azelanitrile | 5.92 | 33.0 | 5.57 |

TABLE 6

Activity of Amycolatopsis in comparison to *Rhodococcus rhodochrous* J1

| | Microorganism Amycolatopsis NA40 (DSMZ 11617) (μmol/ml/min) | Microorganism *Rhodococcus rhodochrous* J1 | Purified enzyme from NA40 (μmol/min/mg protein) | Purified enzyme from J1 (μmol/min/mg protein) |
|---|---|---|---|---|
| Activity for 3-cyanopyridine | 303 | 314 | 1110 | 371 |

(3) For determination of the activity of NA40 with respect to a number of substrates, cells having a dry weight of 0.0388 mg were incubated in the buffer described above. The reaction was started by addition of the appropriate substrate and incubated at 20° C. with shaking for 10 min. The reaction was stopped by addition of 0.2 ml of 2 N HCl and the reaction mixture was briefly centrifuged. The supernatant was analysed by means of HPLC or gas chromatography. Table 8 shows the test conditions for the substrate specificity and Table 9 shows the substrate specificity of resting NA40 cells for various substrates.

The respective test conditions are summarized in Table 8 and the results are summarized in Table 9.

TABLE 7

Effect of the growth temperature on the nitrile hydratase activity and on the cell growth

| Temperature | Growth (mg/ml) | Total activity (μmol/ml/min) | Specific activity (μmol/ml/min/mg) | Relative activity (%) |
|---|---|---|---|---|
| 37° C. | 6.16 | 4.69 | 0.761 | 100 |
| 40° C. | 5.79 | 9.89 | 1.71 | 225 |
| 45° C. | 6.56 | 4.83 | 0.736 | 97 |
| 50° C. | 5.96 | 1.16 | 0.195 | 26 |

TABLE 8

Test conditions for substrate specificity

| Substrate | Substrate (mM) | Analysis method | Amide formed |
|---|---|---|---|
| 3-Cyanopyridine | 1.0 | HPLC | Nicotinamide |
| 2-Cyanopyridine | 0.25 | HPLC | 2-Picolinamide |
| 4-Cyanopyridine | 0.25 | HPLC | Pyridine-4-carboxamide |
| Crotononitrile | 0.4 | HPLC | Crotonamide |
| Benzonitrile | 0.03 | HPLC | Benzamide |
| Acrylonitrile | 0.4 | HPLC | Acrylamide |
| o-Chlorobenzonitrile | 0.15 | HPLC | o-Chlorobenzamide |
| m-Chlorobenzonitrile | 0.15 | HPLC | m-Chlorobenzamide |
| p-Chlorobenzonitrile | 0.15 | HPLC | p-Chlorobenzamide |
| 2-Chloro-3-Cyanopyridine | 0.15 | HPLC | 2-Chloro-nicotinamide |
| Acetonitrile | 0.4 | GC | Acetamide |
| Propionitrile | 0.4 | GC | Propionamide |
| Methacrylonitrile | 0.4 | GC | Methacrylamide |
| n-Butyronitrile | 0.4 | GC | n-Butyramide | o-, m-, p-Chlorobenzonitrile and 2-chloro-3-cyanopyridine were added to the reaction mixture dissolved in methanol.

TABLE 9

Substrate specificity of NA40 nitrile hydratase

| Substrate | Relative activity (%) |
|---|---|
| 3-Cyanopyridine | 100 |
| 4-Cyanopyridine | 168 |
| 2-Cyanopyridine | 128 |
| Benzonitrile | 51 |
| Crotononitrile | 52 |
| Acrylonitrile | 115 |
| o-Chlorobenzonitrile | 96 |
| m-Chlorobenzonitrile | 75 |
| p-Chlorobenzonitrile | 16 |
| 2-Chloro-3-cyanopyridine | 126 |
| Acetonitrile | — |
| Propionitrile | 105 |
| Methacrylonitrile | 130 |
| n-Butyronitrile | 194 |

(4) Temperature optimum and thermal stability in resting cells

The reaction was carried out in the standard reaction mixture for 10 min. The temperature optimum was between 35 and 40° C. (FIG. 5). The cells were then incubated at various temperatures for 30 min and the activity was tested under standard reaction conditions. As can be seen from FIG. 4, the heat stability was 40° C.

(5) pH Optimum and pH Stability in Resting Cells

For this purpose, the reaction was carried out for 10 min in the standard reaction mixture in which the potassium phosphate buffer had been replaced by various 0.1 M buffers. As can be seen from FIG. 6, the pH optimum was between 4.5 and 10. After the cell suspension had been incubated at 20° C. for 30 min at various pHs, the cells were centrifuged. The cells were then washed and resuspended in 0.1 M potassium phosphate buffer pH 7.0. The reaction was carried out for 10 min by addition of 3-cyanopyridine under standard conditions. The enzyme was stable between pH 4.5 and pH 10.0 (FIG. 7).

(6) Accumulation of nicotinamide from 3-cyanopyridine by means of NA40

The reaction was carried out in a reaction mixture (30 ml), comprising 500 mM 3-cyanopyridine, 40 mM potassium phosphate buffer (pH 7.0) and resting cells (dry weight 2.3 mg). During the reaction, 3-cyanopyridine (500 mM) was added 7 times as soon as it was consumed. In this manner, 4.0 M 3-cyanopyridine was added in the course of 15 h and 3.89 M (475 g/l) nicotinamide was formed, corresponding to a yield of 97.3%. Nicotinic acid was not formed.

Example 3

Identification of Microorganisms of the Genus Amycolatopsis

The following 5 chemotaxonomic markers supported the identification:
1. Diagnostic amino acid of the peptidoglycan: mesodiaminopimelic acid
2. Diagnostic sugars: arabinose and galactose
3. Mycolic acids: mycolic acids absent
4. Menaquinones: MK-9 ($H_4$)
5. Fatty acid pattern: iso/anteiso-branched and 2-hydroxy fatty acids, small amounts of 10-methyl-branched fatty acids were additionally detected. This fatty acid pattern was found in all representatives of the genus Amycolatopsis (fatty acid pattern 3f)

The combination of these chemical features is diagnostic of all species of the genus Amycolatopsis.

The fatty acid data of the two cultures were compared with the aid of main component analyses using the entries in the fatty acid database. Using this method, it was possible to assign both NE31 and NA40 to the genus Amycolatopsis, an identification of the species, however, was not possible, since the correlation factor was too low. The comparison of the fatty acid patterns of both strains showed, however, that they are two strains of different types.

The result was confirmed by the results of the 16S rDNA sequence analysis.) Here too, assignment to the genus Amycolatopsis took place, but not to any of the Amycolatopsis species described. In this method, the sequence of the 16S rDNA was determined by the direct sequencing of the PCR-amplified 16S rDNA gene. The diagnostic part of the 16S rDNA sequence was compared with the sequences of the type species of the genus Amycolatopsis and related taxa. The result showed that the strain belongs to the genus Amycolatopsis. The highest agreement was found to Amycolatopsis methanolica at 96.9% (NA40) and 96.1% (NE31). Between them, the two isolates showed agreement in the sequences of 99.0%. Our investigations on representatives of the genus Amycolatopsis have shown that for a good species identification the correlation factor must be higher than 99.5%. Since at 96.9% the value is clearly below 99.5%, it can be assumed from this that the two isolates were not representatives of known Amycolatopsis species.

On the basis of the present results, it was not possible to assign the isolates to any of the known Amycolatopsis species. We assume from this that NA40 and NE31 are strains of two new, previously undescribed species of the genus Amycolatopsis.

Identification Characteristics of Microorganisms of the Genus Amycolatopsis
Colour of aerial mycelium
Colour of substrate mycelium
Colour of diffused pigment

| Sugar spectrum | |
|---|---|
| ARA | + |
| GAL | + |
| MAD | − |
| XYL | − |
| GLU | v |
| RIB | + |
| Type | A |
| DAP | DL |
| Menaquinones (in %) | |
| 8/4 | − |
| 9/0 | (+) |
| 9/2 | + |
| 9/4 | +++ |
| 9/6 | − |
| 9/8 | − |
| 16S rDNA homology | >99.5% |
| Phospholipids | |
| PE | + |
| OH-PE | + |

-continued

| | |
|---|---|
| lyso PE | − |
| met PE | − |
| PC | − |
| NPG | − |
| PI | + |
| PIM | v |
| PG | + |
| DPG | + |
| GL | − |
| Type | II + OH-PE |
| Fatty acids | |
| iso 16 | +++ |
| iso 15 | + |
| iso 17 | (+) |
| anteiso 15 | + |
| anteiso 17 | (+) |
| 10-Me 16 | (+) |
| 10-Me 17 | + |
| 2-OH 15 | + |
| 2-OH 16 | + |
| Type | 3f |
| MS | − |

Example 4

Purification of the Nitrile Hydratase from Microorganism Strain NA40

The strain was cultured at 37° C. for 3 days in the medium according to Table 3. The cells of a 2 l culture were harvested by means of centrifugation and then resuspended in 0.85% strength NaCl solution. The cells were then transferred to 0.1 M potassium phosphate buffer (pH 7.0) comprising 44 mM n-butyric acid and treated with ultrasound. The cell extract was centrifuged and the cell fragments were removed. This extract was used for the enzyme purification.

During the entire purification, potassium phosphate buffer (pH 7.0) comprising 44 mM n-butyric acid was used. As can be seen from Table 10, the enzyme was purified to homogeneity in 3 steps.

TABLE 10

Purification of the nitrile hydratase from NA40

| | Total activity (Units) | Total protein (mg) | Specific activity (U/mg) | Enrichment |
|---|---|---|---|---|
| Cell-free extract | 73,300 | 1020 | 71.9 | 1 |
| DEAE-Sephacel | 68,000 | 110 | 620 | 8.62 |
| Phenyl-TOYOPEARL | 64,800 | 61.4 | 1105 | 15.4 |

1 Unit: The amount of enzyme which catalyses the formation of 1 μmol of nicotinamide/min at 20° C.

Example 5

Characterization of the Nitrile Hydratase (1) Determination of the molecular weight, the subunit structure and the cobalt ion content The molecular weight was determined to be 106 kDa by chromatography on a TSK gel column G3000 SW (0.75×60 cm) using a 0.1 M potassium phosphate buffer (pH 7.0) containing 0.2 M KCl and 44 mM n-butyric acid. It was determined that the enzyme consists of 2 different subunits α and β, whose molecular weight was determined to be 30,000 and 26,000 in each case.

(2) Substrate Specificity of the Purified Enzyme

The substrate specificity was determined analogously to Example 2 (1). The results are summarized in Table 11.

TABLE 11

Substrate specificity of the purified nitrile hydratase

| Substrate | (M) | Total activity (μmol/ml/min) | Relative activity (%) Enzyme reaction | Relative activity (%) Reaction with resting cells |
|---|---|---|---|---|
| 3-Cyanopyridine | 1.0 | 17.7 | 100 | 100 |
| 2-Cyanopyridine | 0.25 | 39.1 | 221 | 128 |
| 4-Cyanopyridine | 0.25 | 31.6 | 179 | 168 |
| Crotononitrile | 0.4 | 11.9 | 67 | 52 |
| Benzonitrile | 0.03 | 11.3 | 64 | 51 |
| Acrylonitrile | 0.4 | 16.6 | 94 | 115 |
| o-Chlorobenzo-nitrile | 0.15 | 22.4 | 127 | 96 |
| m-Chlorobenzo-nitrile | 0.15 | 15.9 | 90 | 75 |
| p-Chlorobenzo-nitrile | 0.15 | 2.30 | 13 | 16 |
| 2-Chloro-3-Cyanopyridine | 0.15 | 16.0 | 90 | 126 |
| Acetonitrile | 0.4 | — | — | — |
| Propionitrile | 0.4 | 39.3 | 222 | 105 |
| Methacrylo-nitrile | 0.4 | 22.1 | 125 | 130 |
| n-Butyronitrile | 0.4 | 17.9 | 101 | 194 |

1.7 Units of enzyme were added to the reaction mixture (2.0 ml). The reaction mixture contained the respective substrate in 45 mM phosphate buffer (pH 7.0).

(3) Determination of the $K_M$ Value

The $K_M$ value was determined to be 41.7 mM for 3-cyanopyridine and to be 3.7 mM for acrylonitrile by means of the Lineweaver-Burk diagram. Compared with *Rhodococcus rhodochrous* J1, which had a $K_M$ value relative to 3-cyanopyridine of 200 mM, that of NA40 is significantly lower. This is one of the main advantages of NA40.

(4) Heat Stability and Temperature Optimum

Figure 1:
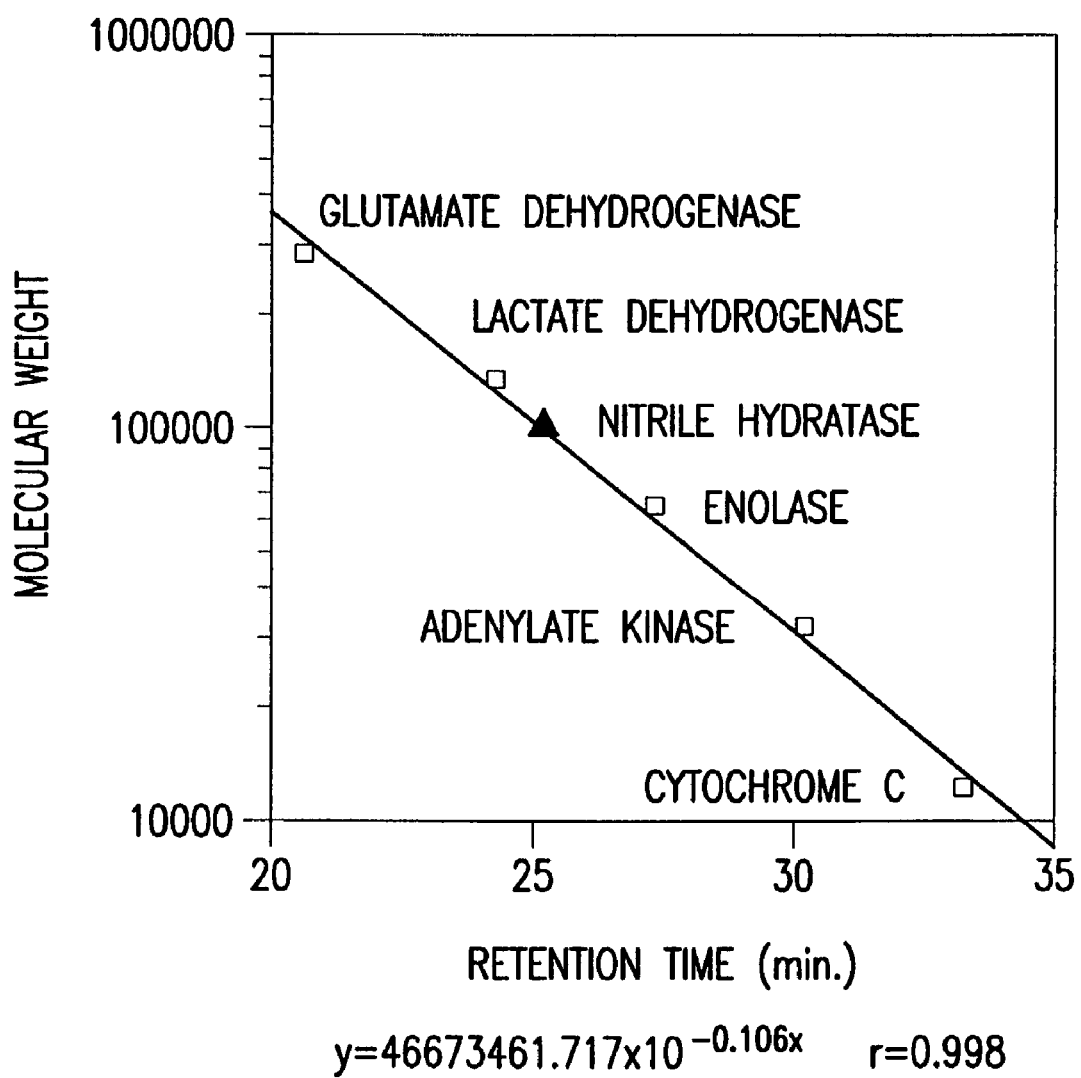
FIG. 1 shows the determination of the molecular weight by chromatography on TSK gel G3000 SW.
Figure 2:
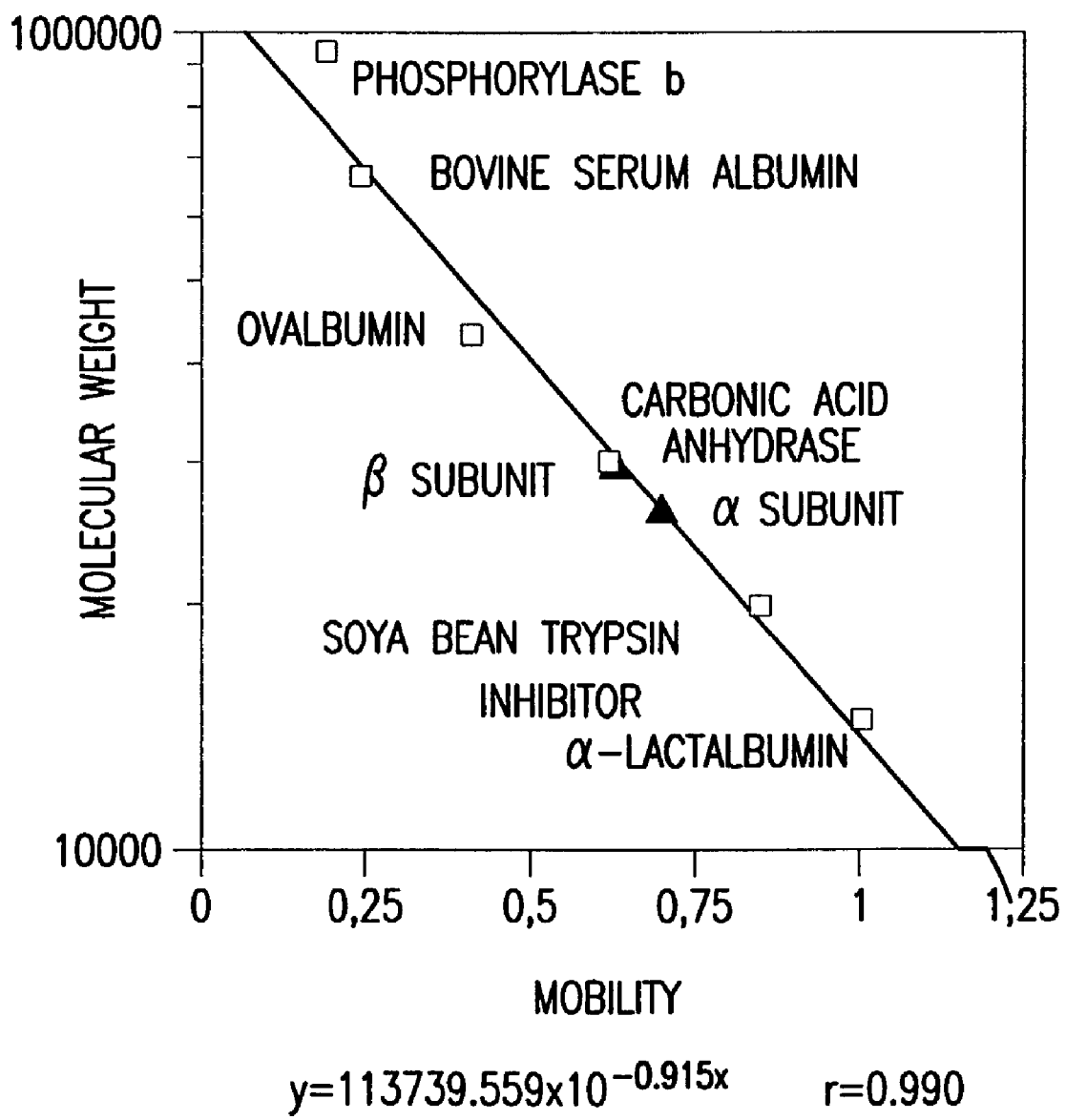
FIG. 2 shows the determination of the molecular weight by means of SDS-PAGE
Figure 3A:
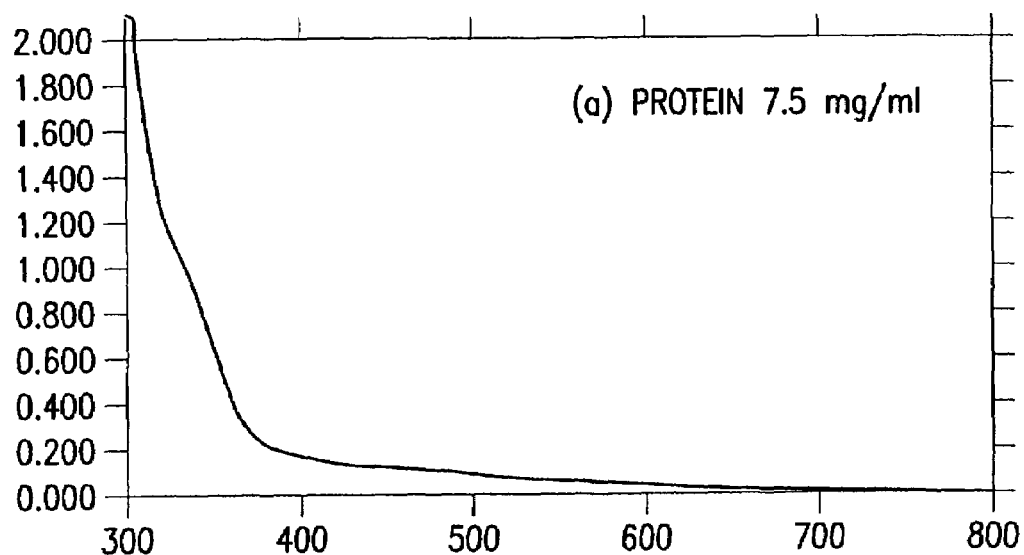
FIG. 3 shows the absorption spectrum of the purified enzyme. A broad absorption of 300–400 nm was observed.
Figure 3B:
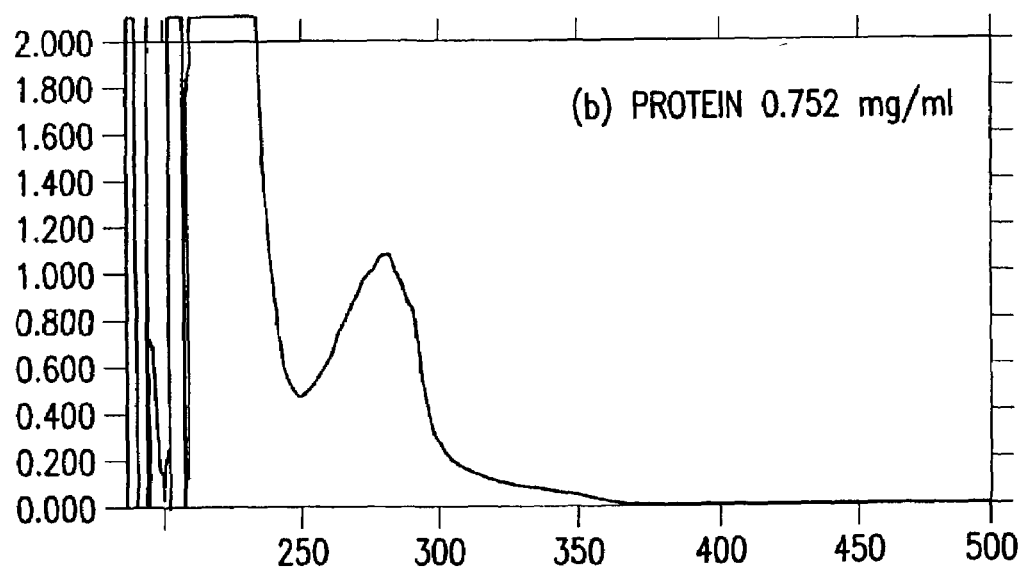
Figure 4:
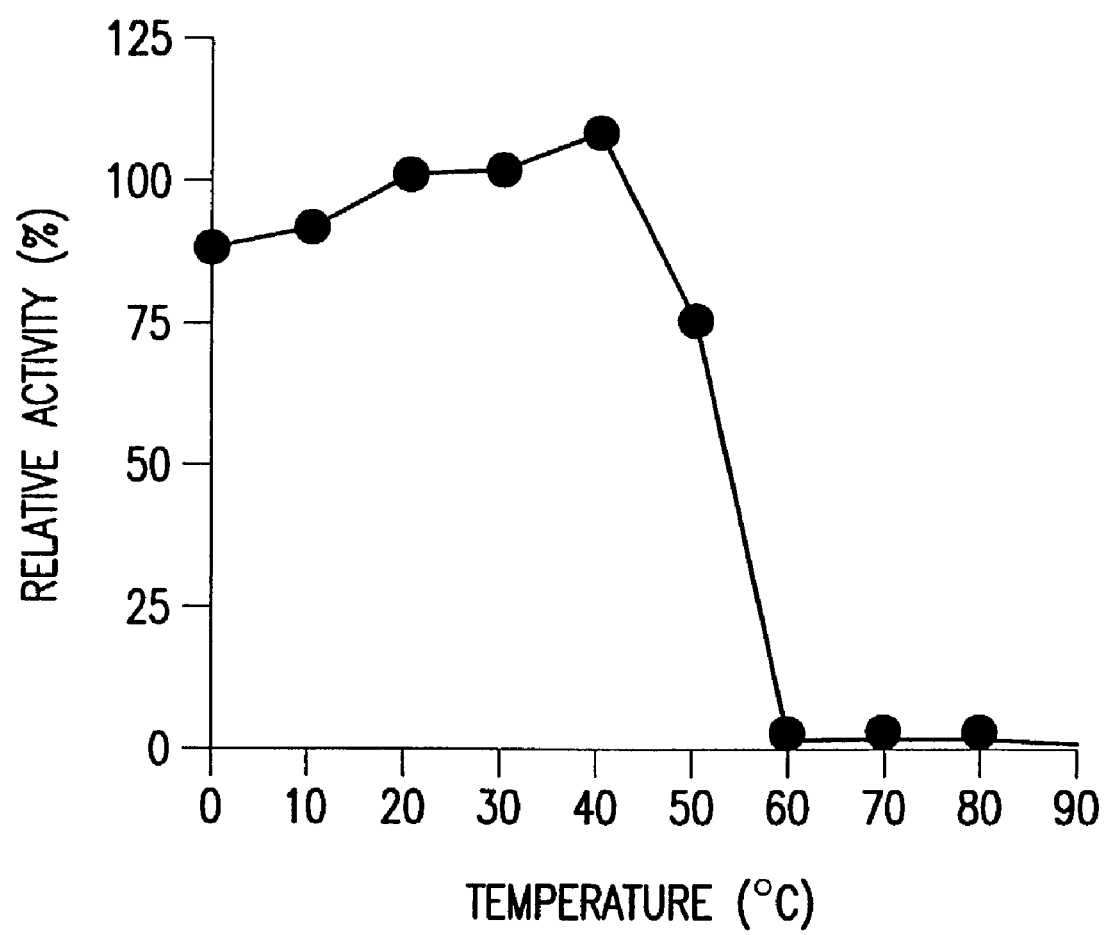
Figure 5:
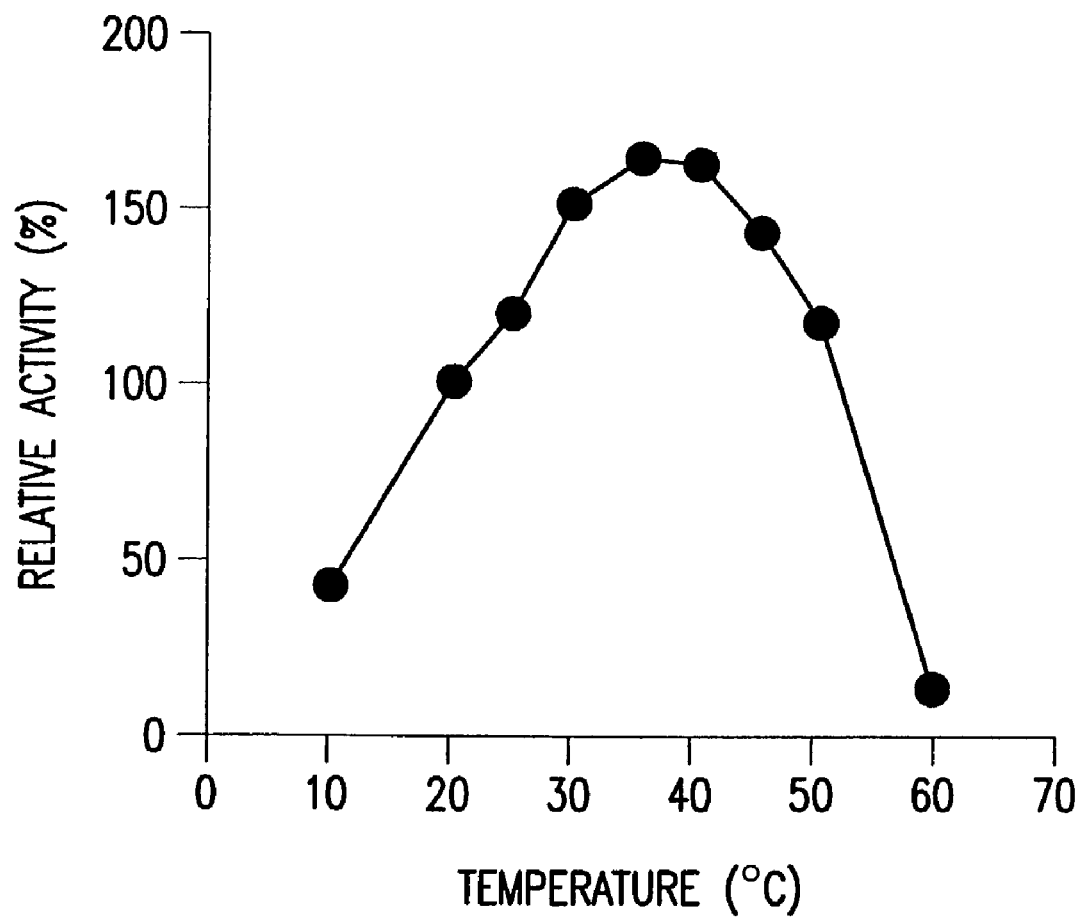
Figure 6:
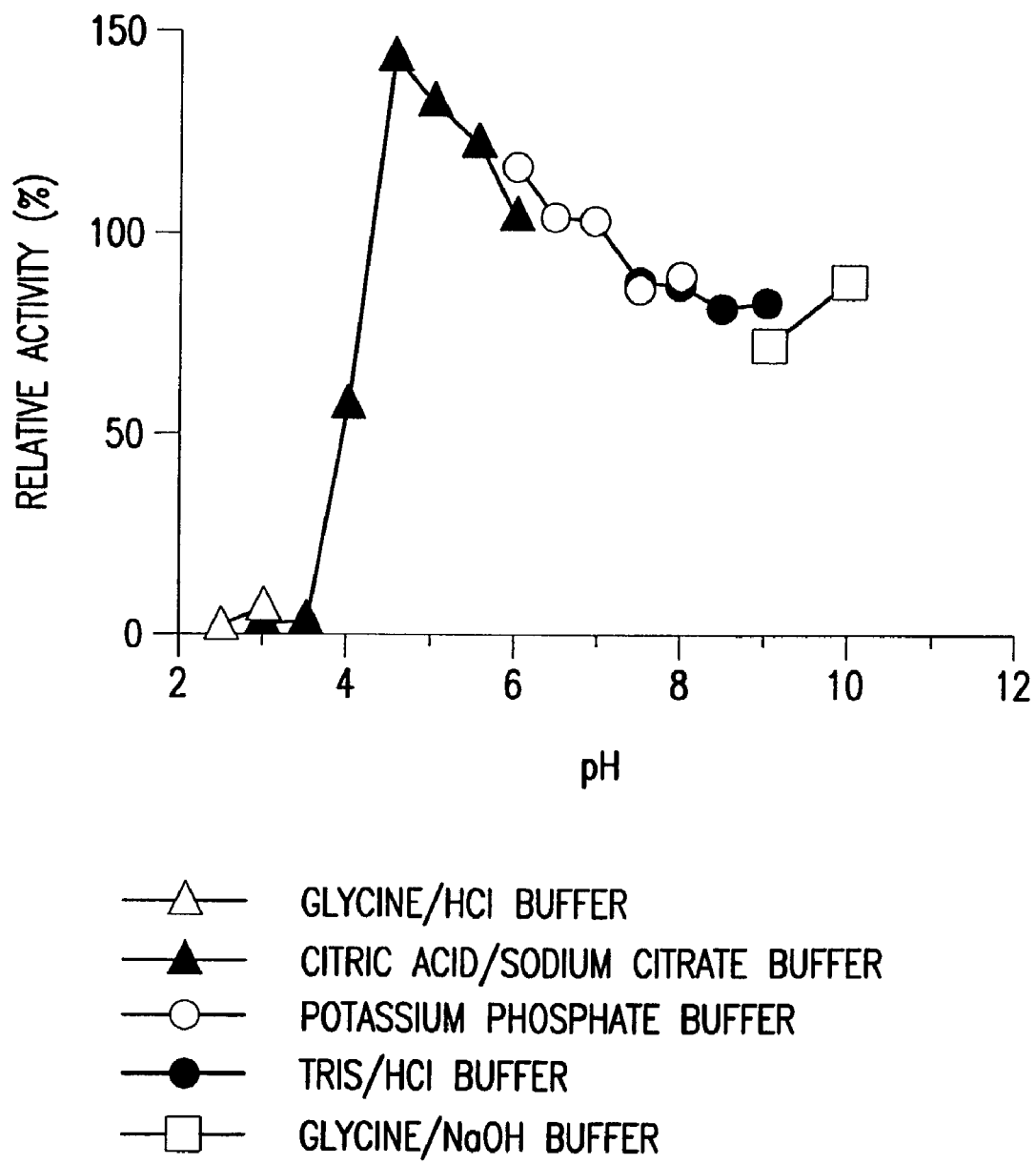
Figure 7:
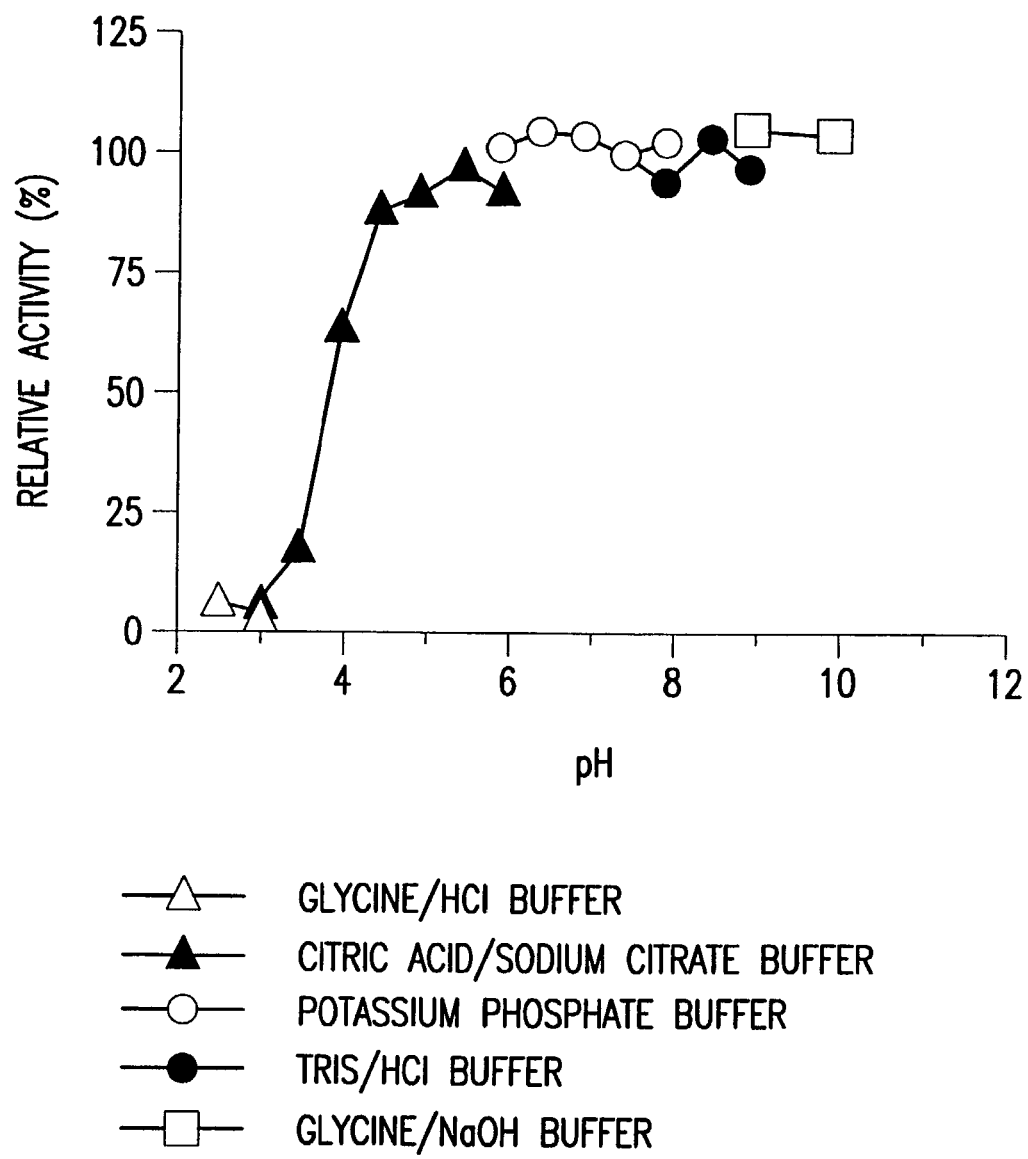

The purified enzyme was incubated for 30 min at pH 7.0 at different temperatures and the conversion of 3-cyanopyridine to nicotinamide was then measured at 20° C. for 1 min. The enzyme was inactivated at a temperature of greater than 40° C. The heat stability was about 40° C. as in resting cells and the temperature optimum was between 35 and 40° C. (FIG. 5).

(5) pH Optimum and pH Stability

Figure 8:
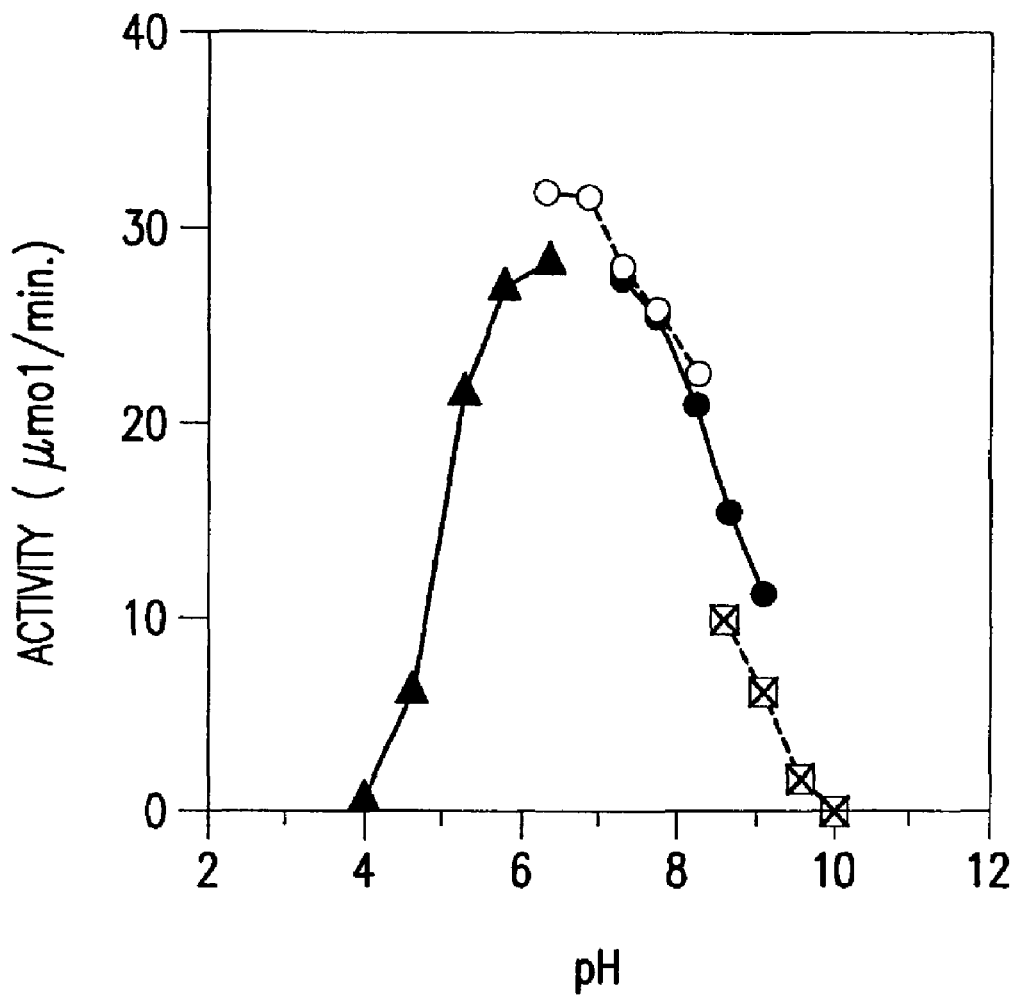

For this purpose, the conversion of 3-cyanopyridine to nicotinamide was carried out at 20° C. in a reaction mixture (2.0 ml) comprising various buffers (42.5 mM), 1.71 units of purified enzyme and 500 mM 3-cyanopyridine. The pH optimum was at about pH 6.5±1.0 (FIG. 8).

Figure 9:
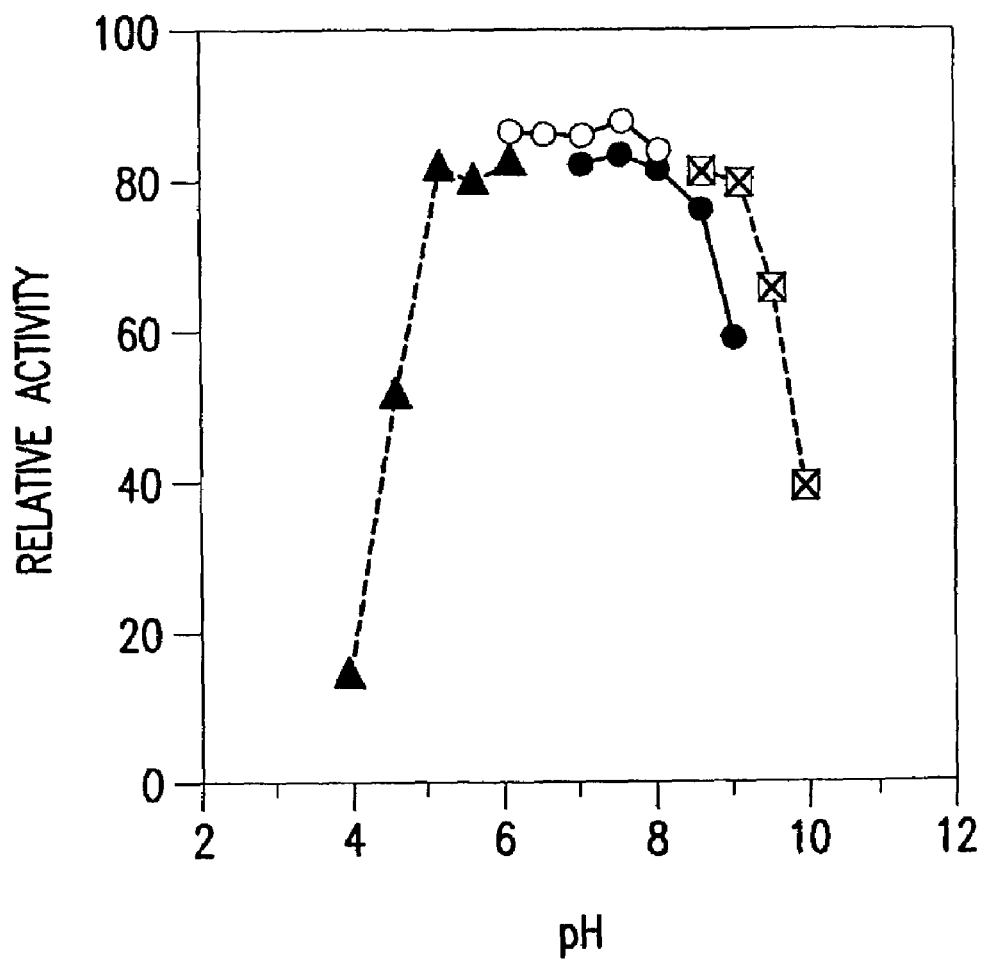

For determination of the pH stability, 4.2 units of purified enzyme were incubated at 20° C. for 1 h in various buffers (45 mM). A part of the incubated solution, 1.71 units, were added to the standard reaction mixture (cf. Example 2(1)). The remaining activity was determined. The enzyme was stable in a pH range from pH 5–9. The result is shown is FIG. 9.

(6) Inhibitors

The effect of various inhibitors was determined. The results are summarized in Table 12.

TABLE 12

Effect of various inhibitors on the purified enzyme

| Inhibitor | mM | Relative activity (%) |
|---|---|---|
| — | | 100 |
| N-ethylmaleimide | 1 | 97 |
| Iodoacetic acid | 1 | 39 |
| 4-Chloromercurobenzoic acid | 0.1 | 69 |
| Sodium azide | 1 | 59 |
| Hydroxylamine | 1 | 37 |
| Phenylhydrazine | 1 | 8 |
| Semicarbazide | 1 | 82 |
| Tiron (disodium salt of 4,5-dihydroxy-1,3-benzene-disulphonic acid | 1 | 110 |
| o-Phenanthroline | 1 | 89 |
| α,α'-Dipyridyl | 1 | 100 |
| 8-Hydroxyquinoline | 1 | 110 |
| EDTA (ethylenediaminetetraacetic acid | 1 | 115 |
| Diethyl dithiocarbamate | 1 | 89 |

Example 6

Effect of Methanol on Resting Cells of NA40

The reaction was carried out for 10 min in the presence of 0–20% (v/v) methanol according to Table 13. As shown in Table 14, the activity is increased by the addition of 5–15% methanol.

TABLE 13

Reaction with resting cells

| | Methods | | | | |
|---|---|---|---|---|---|
| | ① | ② | ③ | ④ | ⑤ |
| 1.0 M 3-cyano-pyridine | 1.0 ml | 1.0 ml | 1.0 ml | 1.0 ml | 1.0 ml |
| 0.1 M KPB* (pH 7.0) | 0.9 ml | 0.8 ml | 0.7 ml | 0.6 ml | 0.5 ml |
| Methanol | — | 0.1 ml | 0.2 ml | 0.3 ml | 0.4 ml |
| Cell suspension (0.388 mg/ml) | 0.1 ml | 0.1 ml | 0.1 ml | 0.1 ml | 0.1 ml |
| Total volume | 2.0 ml | 2.0 ml | 2.0 ml | 2.0 ml | 2.0 ml |

*KPB = potassium phosphate buffer

TABLE 14

Effect of methanol on Amycolatopsis NA40

| Methods | Methanol [% (v/v)] | Relative activity [%] |
|---|---|---|
| ① | 0 | 100 |
| ② | 5 | 123 |
| ③ | 10 | 128 |
| ④ | 15 | 130 |
| ⑤ | 20 | 105 |

Example 7

Enrichment of Microorganisms of the Genus *Rhodococcus*

Various soil samples were inoculated with cyanoacetic acid as a C and N source in the enrichment medium according to Table 1 and the microorganisms *Rhodoccus* GF270, GF578, GF473 and GF376 were isolated according to Example 1.

Example 8

Biotransformation using Microorganisms of the Genus *Rhodococcus*

(1) Heat Stability of the Microorganisms *Rhodoccus* GF674, *Rhodoccus* GF578, *Rhodoccus* GF270 and *Rhodoccus* GF376 in comparison with *Rhodoccus* rhodochrous J1.

For determination of the heat stability, the microorganisms described above were cultured in the following media.

*Rhodococcus rhodochrous* J1 was cultured for 72 h in the medium described in EP-A 0 307 926. The microorganisms *Rhodococcus* GF674, GF578, GF270 and GF376 were cultured in the following media at pH 7.0 for up to 96 h:

*Rhodoccus* GF674 in a medium comprising yeast extract 1.0 g/l, fructose 5.0 g/l, malt extract 10.0 g/l, acetamide 5.0 g/l, $KH_2PO_4$ 2.0 g/l, $MgSO_4 \cdot 7H_2O$ 0.5 g/l and $CoCl_2 \cdot 6H_2O$ 10.0 mg. *Rhodoccus* GF578 in a medium containing yeast extract 1.0 g/l, fructose 15.0 g/l, malt extract 10.0 g/l, acetamide 25.0 g/l, $KH_2PO_4$ 2.0 g/l, $MgSO_4 \cdot 7H_2O$ 0.5 g/l and $CoCl_2 \cdot 6H_2O$ 5.0 mg. *Rhodoccus* GF270 in a medium containing yeast extract 12.5 g/l, sodium citrate 5.0 g/l, methacrylamide 7.5 g/l, $KH_2PO_4$ 2.0 g/l, $MgSO_4 \cdot 7H_2O$ 0.5 g/l and $CoCl_2 \cdot 6H_2O$ 30.0 mg. *Rhodoccus* GF376 in a medium containing yeast extract 1.0 g/l, sodium citrate 10.0 g/l, malt extract 15.0 g/l, butyramide 7.5 g/l, $KH_2PO_4$ 2.0 g/l, $MgSO_4 \cdot 7H_2O$ 0.5 g/l and $CoCl_2 \cdot 6H_2O$ 15.0 mg.

The resting cells were then incubated for 15 min at various temperatures and the remaining activity was then determined under the standard reaction conditions according to Example 2(1).

In the course of this it was found that *Rhodoccus* GF674 had a relative activity of nearly 100% at a temperature of 50° C. and still approximately an activity of 10% at 60° C. *Rhodoccus* GF578 likewise had 100% relative activity at 50° C. and a relative activity of 20% at 60° C. *Rhodoccus* GF376 had 100% relative activity up to 50° C., 70% relative activity at 60° C. and nearly still 5% relative activity at 70° C. *Rhodoccus* GF270 had a relative activity of nearly 100% up to 60° C. and likewise still 5% relative activity at 70° C. In comparison to this, *Rhodoccus* rhodochrous J1 had 100% relative activity up to 50° C., 80% at 60° C. and no longer any activity at 70° C.

In summary, it can therefore be stressed that *Rhodoccus* GF270 and GF376 had a better heat stability than J1 and GF270 had the best heat stability.

(2) pH Optimum of the *Rhodococcus* Strains

The effect of the pH on the nitrile hydratase activity of the *Rhodococcus* strains GF674, GF578, GF270 and GF376 was determined as described in Example 2(5).

The pH optimum of *Rhodoccus* GF674 was at pH 7.5–9.5, of GF578 at pH 8–8.5, for GF270 at pH 6–7.0 and for GF376 at pH 6–8.

(3) Substrate Specificity of the *Rhodococcus* Strains

The substrate specificity is summarized as relative activity in Table 15.

(4) Nicotinamide Accumulation of the *Rhodococcus* Strains

Analogously to Example 2(6), the *Rhodococcus* strains GF674, GF578, GF270 and GF376 were cultured with 3-cyanopyridine (about 500 mM). In the course of this *Rhodoccus* GF674 formed 6 M nicotinamide within 25 h, GF578 5.5 M nicotinamide within 10 h, GF270 about 8.5 M nicotinamide within 20 h and GF376 7.5 M nicotinamide within 20 h.

(5) Tolerance of 3-cyanopyridine on the activity of the *Rhodococcus* strains

In order to test the tolerance of 3-cyanopyridine, resting cells were incubated for 15 min at 20° C. at concentrations of 3-cyanopyridine between 1 and 10% (w/v) and the cells were then removed by centrifugation. After washing the cells with 0.85% NaCl, the remaining activity was measured.

The tolerance of 3-cyanopyridine as a substrate was tested at various substrate concentrations. It was found that at a substrate concentration of 2% (w/v) the nitrile hydratase activity of *Rhodoccus* rhodochrous J1 decreased by the factor 1.4, the nitrile hydratase activity of *Rhodoccus* GF674 at a substrate concentration of 4% (w/v) decreased by the factor 1.4, the nitrile hydratase activity of *Rhodoccus* GF578 remained nearly constant up to a substrate concentration of 8%, the nitrile hydratase activity of *Rhodoccus* GF270 at a substrate concentration of 4% (w/v) decreased by the factor 1.17 and the nitrile hydratase activity of *Rhodoccus* GF376 at a substrate concentration of 10% (w/v) decreased by the factor 1.25.

In comparison with the other *Rhodoccus* strains, *Rhodococcus rhodochrous* Ji exhibited the poorest tolerance for 3-cyanopyridine.

TABLE 15

| | Rhodococcus rhodochrous J1 | Rhodococcus GF674 | Rhodococcus GF578 | Rhodococcus GF270 | Rhodococcus GF376 |
|---|---|---|---|---|---|
| 3-Cyanopyridine | 100 (%) | 100 (%) | 100 (%) | 100 (%) | 100 (%) |
| 2-Cyanopyridine | 45 | 308 | 200 | 15.7 | 54.3 |
| 4-Cyanopyridine | 70 | 231 | 167 | 55.6 | 79.8 |
| Benzonitrile | 27 | 138 | 85.1 | 13.4 | 57.2 |
| 2-Chlorobenzonitrile | 2.8 | 64.8 | 49.0 | 0 | 0 |
| 3-Chlorobenzonitrile | 43 | 27.8 | 28.9 | 8.41 | 8.63 |
| 4-Chlorobenzonitrile | 13 | 0 | 0 | 0 | 0 |
| Acetonitrile | 608 | 1.49 | 347 | 659 | 806 |
| Propionitrile | 434 | 274 | 132 | 37.3 | 245 |
| n-Butyronitrile | 352 | 491 | 368 | 181 | 195 |
| Acrylonitrile | 478 | 147 | 101 | 192 | 257 |
| Crotononitrile | 78.2 | 98.0 | 124 | 37.1 | 110 |
| Methacrylonitrile | 86.9 | 176 | 122 | 0 | 0 |

The invention claimed is:

1. An isolated microorganism of the species *Rhodoccus* GF270 as deposited in the Deutschen Sammlung von Mikroorganismen und Zeilkulturer GmbHand and having accession number DSM 12211.

2. A microorganism which is a mutant of the microorganism of claim 1 which is capable of converting a nitrile into an amide.

3. An isolated microorganism of the species *Rhodoccus* GF376 as deposited in the Deutschen Sammlung von Mikroorganismen und Zeilkulturer GmbHand and having accession number DSM 12175.

4. A microorganism which is a mutant of the microorganism of claim 3 which is capable of converting a nitrite into an amide.

5. A process for the preparation of amides, comprising converting a nitrile, as substrate, to the corresponding amide by means of an agent selected from the group consisting of a microorganism of the species *Rhodoccus* GF270 and a mutant thereof.

6. A process for the preparation of amides, comprising converting a nitrile, as substrate, to the corresponding amide by means of an agent selected from the group consisting of a microorganism of the species *Rhodoccus* GF376 and a mutant thereof.

7. A process according to claim 5 or 6, wherein the nitrite employed is an optionally substituted aliphatic nitrile having 1 to 10 carbon atoms.

8. A process according to claim 5 or 6, wherein the nitrile employed is an optionally substituted aromatic nitrile having 4 to 10 carbon atoms in the aromatic ring system.

9. A process according to claim 8, wherein the aromatic nitrile is selected from the compounds of the general formula

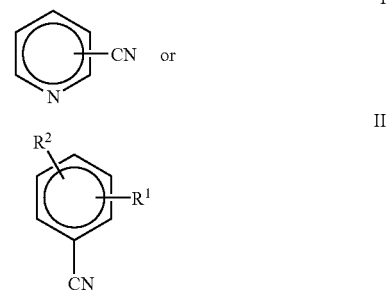

in which $R^1$ and $R^2$ are a hydrogen atom, a halogen atom or $C_{1-4}$-alkyl.

10. A process according to claim 5 or 6, wherein the reaction is carried out at a temperature from 0 to 50° C. and at a pH from 4.5 to 10.

* * * * *